(12) United States Patent
Saxer et al.

(10) Patent No.: US 9,733,152 B2
(45) Date of Patent: Aug. 15, 2017

(54) IMMERSION LENS ASSEMBLIES FOR USE IN OPTICAL COHERENCE TOMOGRAPHY SYSTEMS

(71) Applicant: Bioptigen, Inc., Morrisville, NC (US)

(72) Inventors: Christopher Saxer, Cary, NC (US); Robert H. Hart, Cary, NC (US); Eric L. Buckland, Hickory, NC (US)

(73) Assignee: Bioptigen, Inc., Morrisville, NC (US)

( * ) Notice: Subject to any disclaimer, the term of this patent is extended or adjusted under 35 U.S.C. 154(b) by 105 days.

(21) Appl. No.: 14/573,339

(22) Filed: Dec. 17, 2014

(65) Prior Publication Data

US 2015/0168250 A1 Jun. 18, 2015

Related U.S. Application Data

(60) Provisional application No. 61/916,948, filed on Dec. 17, 2013, provisional application No. 61/917,521, filed on Dec. 18, 2013.

(51) Int. Cl.
*G01B 11/02* (2006.01)
*G01M 11/02* (2006.01)
(Continued)

(52) U.S. Cl.
CPC ....... *G01M 11/0207* (2013.01); *A61B 5/0066* (2013.01); *G01B 9/02044* (2013.01);
(Continued)

(58) Field of Classification Search
CPC ......... G01M 11/0207; G01M 11/0271; G01M 11/025; A61B 5/0066; A61B 5/0084;
(Continued)

(56) References Cited

U.S. PATENT DOCUMENTS 4,011,446 A * 3/1977 Swanberg ............ G03B 27/522
250/201.4
5,166,756 A * 11/1992 McGee .............. G01N 21/8507
250/227.29
(Continued)

*Primary Examiner* — Tarifur Chowdhury
*Assistant Examiner* — Jonathon Cook
(74) *Attorney, Agent, or Firm* — Ward and Smith, P.A.

(57) ABSTRACT

An optical coherence tomography (OCT) measurement system for precision measurement of a translucent sample is provided. The system includes an optical coherence tomography (OCT) imaging system comprising a broadband light source, a reference path with reference path length, and sample path with a beam scanning assembly and an imaging lens assembly; a sample positioning assembly including an immersion bath for positioning the translucent sample within an immersion bath; a position assembly for locating the translucent sample within a field of view (FOV) of the OCT imaging system; an immersion lens assembly associated with the imaging lens assembly configured to eliminate an air to bath refractive interface between a distal surface of the OCT imaging lens including an immersion tip and a surface of the bath; a first set of calibration parameters that relate a position of a scanning beam at an imaging plane to drive signals of the scanning assembly; and a second set of calibration parameters for relating an optical path length or optical path length variation of the scanning beam at an imaging plane to the position of the scanning beam or to the drive signals of the scanning assembly.

4 Claims, 13 Drawing Sheets

(51) Int. Cl.
*G01B 9/02* (2006.01)
*A61B 5/00* (2006.01)

(52) U.S. Cl.
CPC ..... *G01B 9/02064* (2013.01); *G01B 9/02072* (2013.04); *G01B 9/02091* (2013.01); *G01M 11/025* (2013.01); *G01M 11/0271* (2013.01)

(58) Field of Classification Search
CPC ............ G01B 9/02044; G01B 9/02091; G01B 9/0209; G01Q 60/22; G01N 21/8507; G01N 2021/8528
USPC ........................................ 356/456, 479, 497
See application file for complete search history.

(56) References Cited

U.S. PATENT DOCUMENTS

| | | |
|---|---|---|
| 6,840,632 B2 | 1/2005 | Shyu et al. |
| 8,274,721 B2 | 9/2012 | Cho et al. |
| 8,693,745 B2 | 4/2014 | Izatt et al. |
| 2005/0283065 A1* | 12/2005 | Babayoff ........... A61B 1/00009 600/407 |
| 2007/0265602 A1* | 11/2007 | Mordaunt ............... A61F 9/008 606/4 |
| 2014/0107960 A1 | 4/2014 | Oritz Egea et al. |

\* cited by examiner

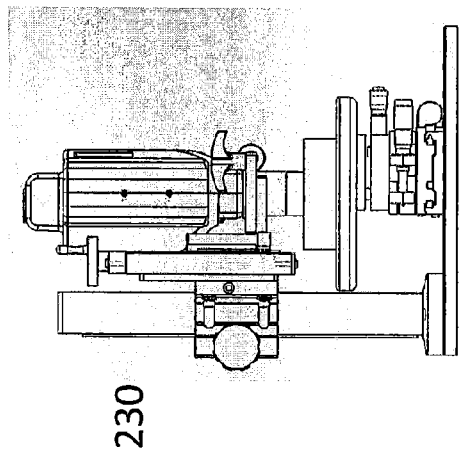
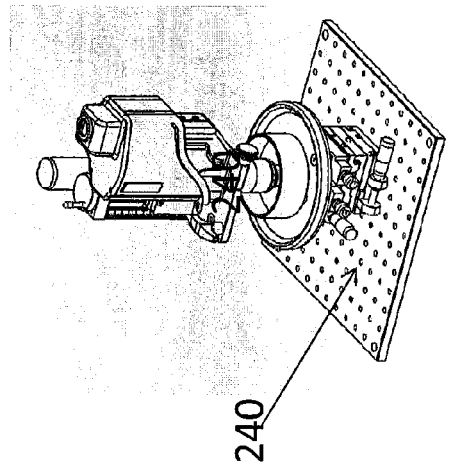
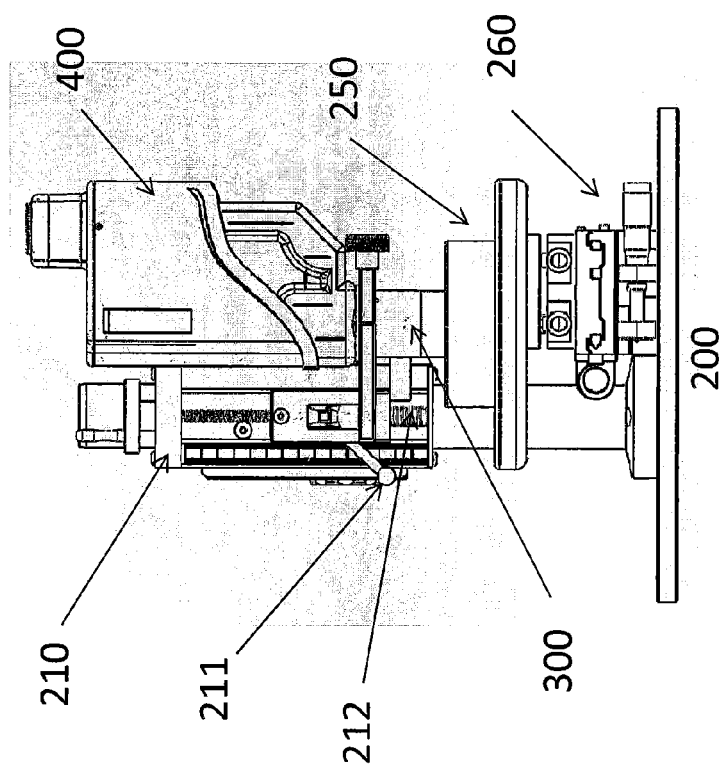
FIG. 2B
FIG. 2C
FIG. 2A

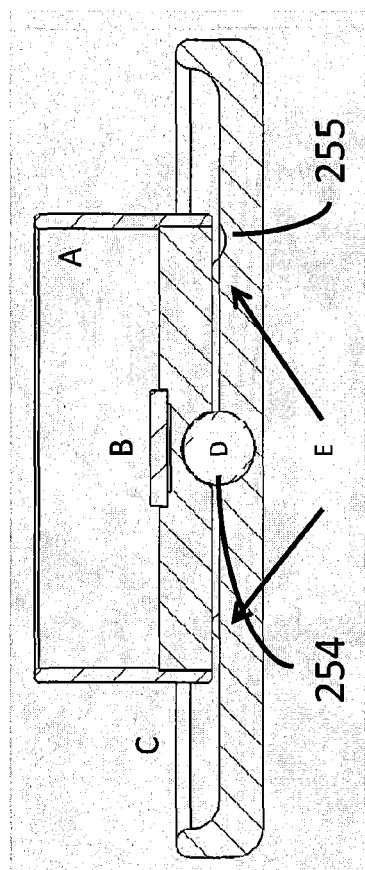
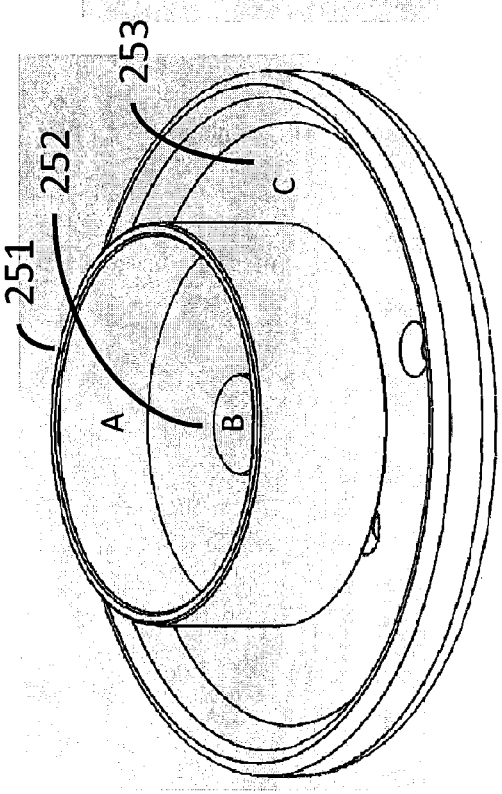
FIG. 5B
FIG. 5A

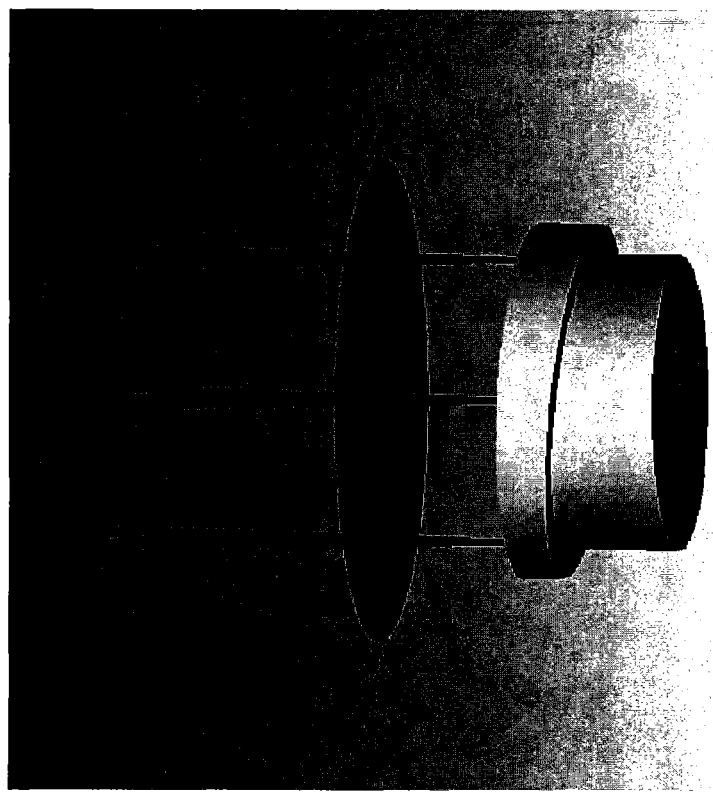
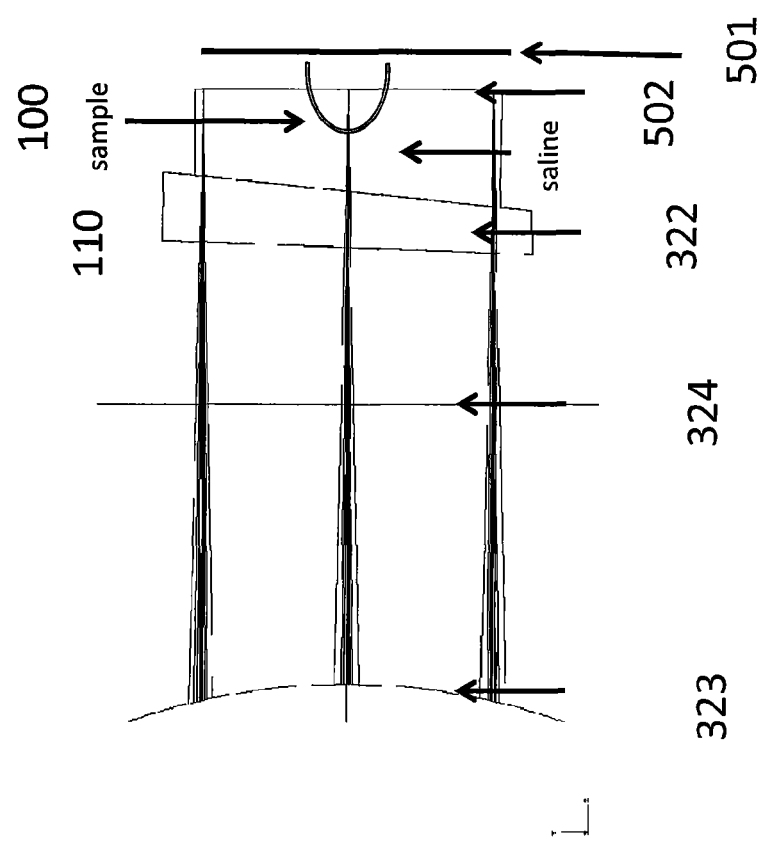
FIG. 6B
FIG. 6A

IMMERSION LENS ASSEMBLIES FOR USE IN OPTICAL COHERENCE TOMOGRAPHY SYSTEMS

CLAIM OF PRIORITY

The present application claims priority to U.S. Provisional Application Ser. No. 61/916,948, filed Dec. 17, 2013 and U.S. Provisional Application Ser. No. 61/917,521, filed Dec. 18, 2013, the disclosures of which are hereby incorporated herein by reference as if set forth in their entirety.

FIELD

The present inventive concept relates generally to the imaging, tomography, topography, and measurement of translucent devices using scanning low coherence interferometry and optical coherence tomography and, more particularly to the imaging and precision metrology of optical lenses, corrective lenses for vision, contact lenses and corneal implants for vision refractive correction, intraocular lenses and the like using optical coherence tomography (OCT).

BACKGROUND

Contact lenses are evolving from simple rotational symmetric spherical design for monofocal correction to much more complex design to correct a broad array of visual defects. Aspheric designs provide greater flexibility in correcting aberrations. Rotationally asymmetric lenses, or torics, are correcting astigmatism. Higher order deviations from sphericity and rotational symmetry are now being proposed to go beyond correction to treatment of refractive defects such as myopia. Simple prescriptive parameters of sphere and cylinder are not sufficient for defining the performance of complex refractive correction lens elements.

Optical coherence tomography (OCT) is a well established technique for high resolution volumetric, or tomographic, visualization of translucent materials and biological tissues. OCT is a standard of care in ophthalmic diagnostic imaging, particularly of the retina. OCT systems are generally well characterized for axial or longitudinal resolution. Lateral performance is decoupled from longitudinal performance, and is a function the system optics, including optics of the sample. Precision characterization of lateral and topographic accuracy and precision has not been a requirement for retinal ophthalmology.

Recently, OCT is being studied for characterization of the anterior segment of the eye, and specifically as an adjunct to other topographic diagnostic systems, such as placido rings. With the ability to characterize multiple surfaces in the cornea and the crystalline lens, OCT offers the potential to compute clinical parameters, including refractive power astigmatism, as well as higher order aberrations. Computation of clinical parameters requires an increase in accuracy and precision in both longitudinal and lateral dimensions, as discussed in, for example, U.S. Patent Publication No. 2014/017960 to Egea and U.S. Pat. No. 8,693,745 to Izatt.

The precision required for anterior segment of the eye can be extended to requirements for measuring refractive correction devices for the eye. As the complexity of refractive correction devices increases, there is commensurate need for increased precision in measuring such devices and in computing the clinically relevant parameters for such devices. Refractive correction devices such as contact lenses, corneal inlays and onlays, intraocular lenses, and donor tissues for cornea transplant have material and structural properties that introduce measurement challenges that have not been addressed with anterior segment OCT.

SUMMARY

Some embodiments of the present inventive concept provide an optical coherence tomography (OCT) measurement system for precision measurement of a translucent sample. The system includes an optical coherence tomography (OCT) imaging system comprising a broadband light source, a reference path with reference path length, and sample path with a beam scanning assembly and an imaging lens assembly; a sample positioning assembly including an immersion bath for positioning the translucent sample within an immersion bath; a position assembly for locating the translucent sample within a field of view (FOV) of the OCT imaging system; an immersion lens assembly associated with the imaging lens assembly configured to eliminate an air to bath refractive interface between a distal surface of the OCT imaging lens including an immersion tip and a surface of the bath; a first set of calibration parameters that relate a position of a scanning beam at an imaging plane to drive signals of the scanning assembly; and a second set of calibration parameters for relating an optical path length or optical path length variation of the scanning beam at an imaging plane to the position of the scanning beam or to the drive signals of the scanning assembly.

In further embodiments, the translucent sample may be a refractive correction element. The refraction correction element may be one of a contact lens, a corneal inlay, a corneal onlay, an intraocular lens, and donor tissues for cornea transplant.

In still further embodiments, the immersion bath may be a fluid.

In some embodiments, the system may be configured to acquire a full lateral range and full depth range image of a contact lens immersed in the immersion bath.

In further embodiments, the OCT system may be a spectral domain OCT (SDOCT) system. The SDOCT system may be a spectrometer including a grating and a prism, a spectral bandwidth of less than or equal to 54 nm and a line scan camera detector array comprising at least 4096 pixels.

Still further embodiments of the present inventive concept provide methods for imaging an artificial lens using an optical coherence tomography (OCT) imaging system. The method includes positioning the artificial lens bezel-side down on a substrate in a bath; and setting a reference arm of the OCT imaging system such that there is a zero path length difference between a reference path and a sample path, the sample path being positioned underneath or behind a bezel.

In some embodiments, an OCT beam focus may be positioned approximately two-thirds of a distance between a central apex and the bezel of the artificial lens, and closer to the bezel.

In further embodiments, a center of the artificial lens may be positioned physically closer to the imaging system than is the bezel.

In still further embodiments, the OCT imaging system may be one of a spectral domain OCT imaging system, a spectrometer-based OCT imaging system and a swept source OCT imaging system In some embodiments, the artificial lens may be a refractive correction lens and wherein the refraction correction lens comprises one of a contact lens, a corneal inlay, a corneal onlay, an intraocular lens, and donor tissues for cornea transplant.

Further embodiments of the present inventive concept provide an immersion lens assembly for obtaining OCT images of samples immersed in a solution. The immersion lens assembly includes a portion of a telecentric or pseudo-telecentric scanning lens assembly; and an immersion tip attached to the scanning lens and configured to be immersed in the solution.

In still further embodiments, the immersion tip includes an optical wedge. The optical wedge may provide a ray passing through the wedge configured to be laterally shifted, but angularly un-deviated; and specular reflections from the wedge reflecting at an angle outside of a numerical aperture of an OCT beam.

In some embodiments, the wedge may have an anti-reflection coating to reduce optical losses at an air-wedge interface and a bath-wedge interface. The wedge may be N-BK7 glass with a refractive index of 1.509, a wedge angle of 3.88 degrees.

BRIEF DESCRIPTION OF THE DRAWINGS

FIGS. 2A-2C are diagrams illustrating front, side and trimetric views, respectively, of a staging system in accordance with some embodiments of the present inventive concept.

FIGS. 5A and 5B are diagrams illustrating a sample holder in accordance with some embodiments of the present inventive concept.

FIGS. 6A and 6B are diagrams illustrating an immersion tip optical layout in accordance with some embodiments of the present inventive concept.

DETAILED DESCRIPTION

Figure 1:
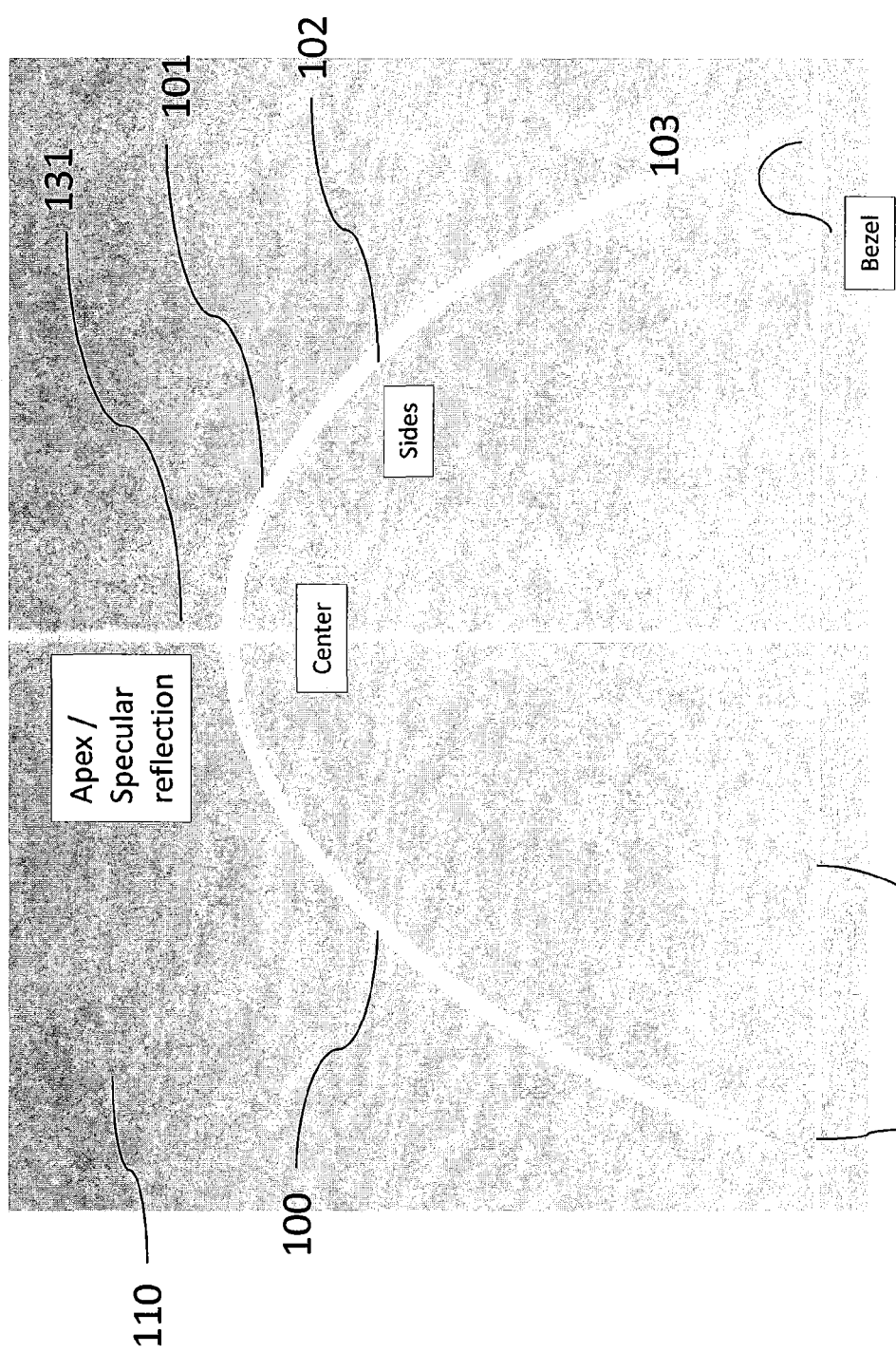
FIG. 1 is a diagram illustrating a contact lens imaged with an optical coherence tomography (OCT) system, reference arm setting and focal position setting in accordance with some embodiments of the present inventive concept.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Although many of the examples discussed herein refer to the sample being a refractive correction lens, specifically, a contact lens, corneal inlays and onlays, intraocular lenses, and donor tissues for cornea transplant, embodiments of the present inventive concept are not limited to this type of sample. As used herein, the terms "artificial lens" or "translucent sample" will refer to any of these samples without departing from the present inventive concept. Any type of sample that may be used in conjunction with embodiments discussed herein may be used without departing from the scope of the present inventive concept.

As discussed above, refractive correction lenses, such as contact lenses, are being designed and produced with increased complexity to improve vision over a wider range of anomalies and to therapeutic purpose to influence the growth of the eye, as in for example, myopia prevention or correction. There is an emerging need to be able to measure and characterize such devices with a greater degree of accuracy and precision than has been required for monofocal correction of focal power and low grade astigmatism.

Contact lenses and the like are difficult to measure with precision for a variety of reasons. They are small, flexible, and highly curved—attributes that don't lend themselves well to mechanical measurements. They tend to have high water content, and should therefore be measured in water to avoid inaccuracies of dehydration. Ultrasound does not have sufficient resolution.

Optical coherence tomography (OCT) has high axial (longitudinal) resolution owing to the coherence gating function of low coherence interferometry. Typical commercial OCT systems have axial resolutions of from about 3.0 to about 6.0 μm. Lateral resolution is dictated by the imaging optics, and is function of the numerical aperture and focal length of the imaging system. Highest lateral resolution is attainable with high numerical aperture and short focal length. Typical OCT systems designed for pseudo-telecentric scanning, as might be used for imaging the anterior segment of the eye or imaging surface tissues have lateral resolution of between about 8.0 and about 20 μm. An example OCT system is discussed below with respect to FIG. 13.

OCT system design represents a tradeoff between longitudinal resolution and depth, and this tradeoff is further complicated when considering metrology over depth. OCT systems have not heretofore been developed for the imaging challenges posed by contact lenses. For example, contact lenses have diameters of 14 millimeters, requiring telecentric imaging over a wide field of view (FOV). A contact lens depth, or sagitta, measured along the axis from the top surface to the bottom of an edge, or bevel, is 4000 to 6000 μm, with thicknesses of 50 to 150 μm. This range of scales presents a challenge to any imaging system. Accurate and precise measurement of contact lens dimensions of even simple contact lenses has not been previously demonstrated.

In order fully characterize a contact lens with OCT, a deep imaging system with a minimal differential signal-to-noise (SNR) fall off over the depth of the lens is required. The longitudinal (axial) resolution should be high enough to image and measure the edges of the lens and interior structures from center to bezel. The FOV should be wider than the diameter of the contact lens. The lateral resolution should be fine enough to image transition zones in the shape of the lens. The system should be calibrated laterally for precise positional location across the FOV. The system should be calibrated for optical path length variations, or differences (OPLD; longitudinal distortion) across the FOV. Segmentation algorithms should be able to find all edges with high precision, and should include robust outlier detection and smoothing algorithms that do not distort the shape of the lens. Segmentation should also account for refraction through all surfaces that occur as a result of refractive index differences at any surface.

A contact lens metrology system should also include a water bath to keep the lens hydrated, and therefore requires OCT imaging optics for imaging samples in a water bath. The physical system for managing the immersed sample should facilitate reproducible placement of sample within the FOV of the OCT imaging system.

Accordingly, some embodiments of the present inventive concept provide an OCT system suitable for full range imaging of a contact lens, or like object, immersed in a saline or other similar bath. In some embodiments, the full range image of the contact lens is obtained in a single imaging pass, without axial image stitching, in order to preserve precision of the image. In these embodiments, a spectral domain OCT system is used featuring a wavenumber-linearized spectrometer. The spectral domain OCT system may include, for example, a spectrometer including a grating followed by a grism (grating-prism pair) to disperse a 54 nm optical spectrum centered at 880 nm onto a 4096 element line scan camera detector array and a detector array including 10 μm square pixels, for an image depth in the spatial domain of 15.3 mm. The system may be optimized to image a contact lens immersed in saline, with a refractive index of 1.343. A contact lens with depth, or sagitta, of 4 mm in air will occupy 5.4 mm of the available image window. The OCT system has a measured SNR fall of approximately 1 dB/mm. The SNR fall off over the depth of the contact lens is, thus, less than 6 dB.

Figure 12:
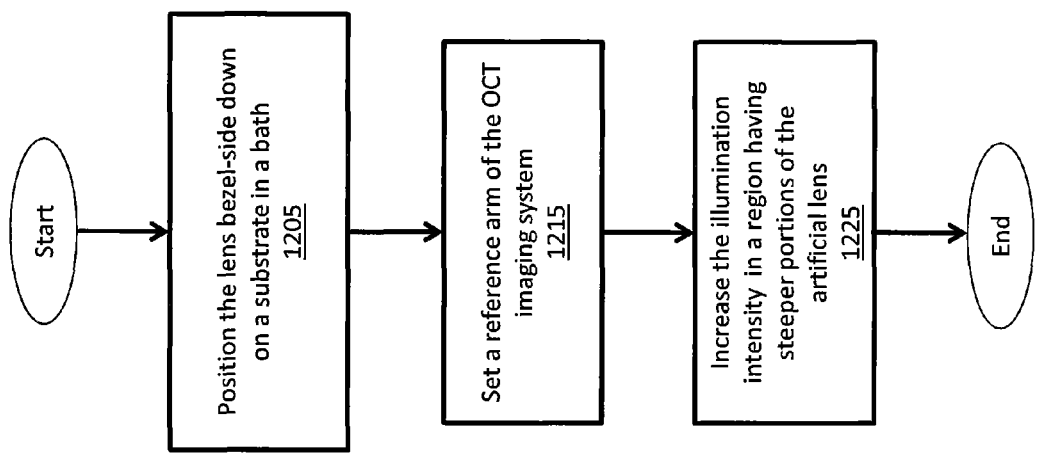
FIG. 12 is a flowchart illustrating operations for imaging an artificial lens in accordance with some embodiments of the present inventive concept.

In some embodiments of the present inventive concept, the illumination of the contact lens is optimized for uniformity and minimization of artifacts. The contact lens, when imaged, has a flat center (the apex) and steep sides. An OCT image will exhibit a specular reflection at the apex, and the signal falls off sharply on the sides as the specular component of reflection falls off with incident angle. A method including three techniques to provide a stable orientation for the lens, reduce specular glare and improve uniformity of illumination may be performed according to the flowchart of FIG. 12.

First, the lens is placed bezel-side to the platform on which the lens rest (block 1205). This keeps the center of the lens from compressing and distorting the shape, and the bezel acts as legs to support the body of the lens.

Second, the reference arm of the OCT system is set such that the zero path length difference between the reference path and the sample path is positioned underneath, or behind the bezel (block 1215). The center of the contact lens is thus closer to the imaging system than the bezel, or further from the zero path length difference condition. Since all Fourier domain OCT systems (spectral domain, or spectrometer-based systems and swept source systems) have a signal-to noise ratio that is a decreasing function of subject distance from the DC, or zero path length, condition, it is desirable to set the lower signal return portion of a subject closer to the zero path length position.

Third, for similar reasons, it is desirable to increase the illuminating intensity in the region of the steeper portions of the lens under test (block 1225). Therefore, the focus is positioned approximately two-thirds of the distance between center and the bezel of the contact lens, closer to the bezel. This balance between path matching and focus may be considered a hyperfocal condition in analogy to traditional photography, where instead of focal uniformity, illumination uniformity is sought.

Referring now to FIG. 1, a diagram illustrating a contact lens imaged with an OCT system, reference arm setting and focal position setting as discussed above will be discussed. As illustrated in FIG. 1, the contact lens 100 is positioned bezel 103 down on a substrate 111 in a saline solution 110. The anterior 101 and posterior 102 surfaces of the contact lens 100 are clear resolved from apex 131 to bezel 103. A specular reflection artifact is present at the apex 131 as a result of normal incidence illumination from the OCT beam. The differential refractive index of the contact lens 100 increases the optical path length to the substrate 111, and a kink 132 in the imaged position of the substrate 111 under the lens as a result of this refractive index difference is visible.

Referring now to FIGS. 2A through 2C, a front, side and trimetric view, respectively, of a staging system for reproducible imaging of a sample immersed in a bath in accordance with some embodiments of the present inventive concept will be discussed. Referring to the front view of FIG. 2A, the staging system includes a fixture 200, a probe mount (Z adjustment) 210, a Z quick release 211, a Z lift spring 212, an immersion tip 300 (20 mm FOV lens), a probe 400, a sample holder (θ adjustment) 250, and a sample positioning stage (X, Y, α and ϕ adjustments) 260. As illustrated, the fixture 200 is for reproducibly imaging an immersed sample. The staging system includes an OCT scan head 400, or probe, to which is attached a wide field telecentric imaging lens with an immersion tip 300. The probe is affixed to a probe mount 210 with a fine vertical (z) adjustment for providing positional accuracy better than or equal to 100 micrometers, and a quick release mechanism 211 and a lift spring 212 for allowing disengagement for the probe from the sample holder. The sample holder 250 is a platform for holding an immersed sample, such as a contact lens. The sample holder sits on a positioning stage 260. The sample holder 250 and positioning stage 260 provide five degrees of freedom for alignment (x,y, alpha (α), phi (ϕ), and theta (θ)). Alpha and phi provide rotation to set the orientation of the sample normal to the incident scanning beam; and theta is rotation of the sample about the incident scanning beam. The degrees of freedom (x, y, alpha, and phi) are used to center the lens, and position normal to the scanning beam. For convenience, the probe mount 210 is attached to a riser pole 230 (FIG. 2B), and the entire assembly is positioned on a base plate 240 (FIG. 2C). When properly aligned the sample can be imaged with near perfect rotational symmetry.

In some embodiments, an immersion tip for obtaining OCT images of objects immersed in a fluid bath may be provided. Imaging directly through the surface of a water bath is not desirable. The surface of the water may create specular reflection artifacts in the OCT image, and these artifacts may not be constant in time if there is any ripple in the surface of the bath. A water surface will also have a meniscus that will distort the path of the scanning beam. Additionally, it may be difficult to maintain a constant bath depth, impacting working distance, focus, path matching conditions, and dispersion compensation. To solve these problems, an immersion lens or tip associated with the OCT imaging lens is desired to break the surface of the immersion bath, eliminate the air to bath refractive interface between the distal surface of the OCT imaging lens including the immersion tip and the surface of the bath, and provide a controlled surface for transmission of the scanning OCT beam into the bath and to the sample.

Figures 3A, 3B:
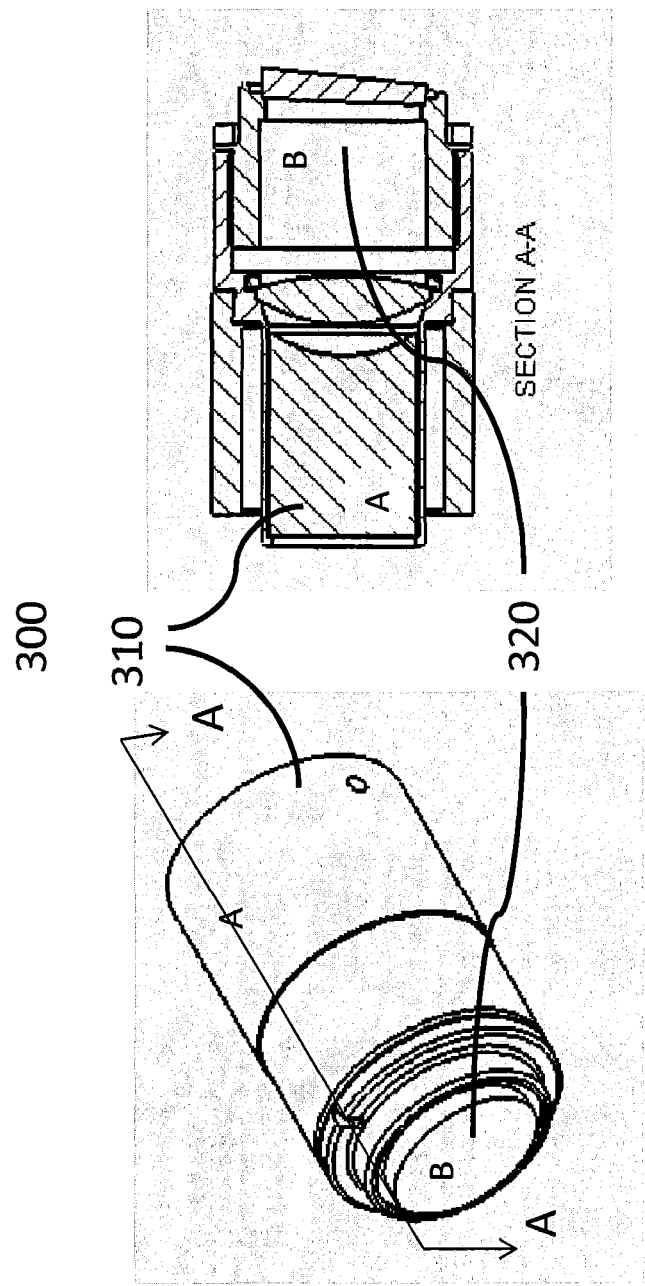
FIGS. 3A and 3B are diagrams illustrating an isometric view and cut away view along the line A-A of FIG. 3A, respectively, of an immersion lens assembly in accordance with some embodiments of the present inventive concept.

Referring now to FIGS. 3A and 3B, an isometric view and cut away view along the line A-A of FIG. 3A, respectively, of an immersion lens assembly will be discussed. As illustrated in FIGS. 3A and 3B, some embodiments of the present inventive concept, provide an immersion tip 300 for a telecentric or pseudo-telecentric (approximately telecentric) scanning lens. As illustrated in FIGS. 3A and 3B, the immersion lens assembly may include a portion of the telecentric scanning lens assembly 310 (portion A) and the immersion tip itself 320 (portion B). The immersion tip includes a precision wedge designed with the following attributes: a) a ray passing through the wedge may be laterally shifted, but angularly un-deviated; and b) specular reflections from the wedge will reflect at an angle outside of the numerical aperture of the OCT beam. The wedge may also be anti-reflection coating to minimize optical losses at the air-wedge interface and the bath-wedge interface. A wedge designed in accordance with some embodiments of the present inventive concept is made from N-BK7 glass with a refractive index of 1.509. The wedge angle is 3.88 degrees, and positioned such that the top surface is at an angle of 2.05 degrees to the OCT beam axis. The bottom surface of the wedge is at an angle of 5.93 degrees to the OCT beam axis.

Figure 4C:
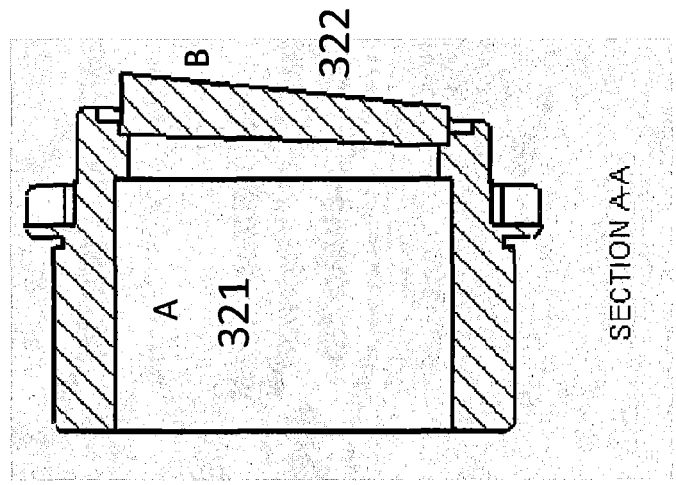
FIGS. 4A-4C are diagrams illustrating an isometric view, a side view and cut away view along the line A-A of FIG. 4B, respectively, of an immersion tip assembly in accordance with some embodiments of the present inventive concept.
Figure 4B:
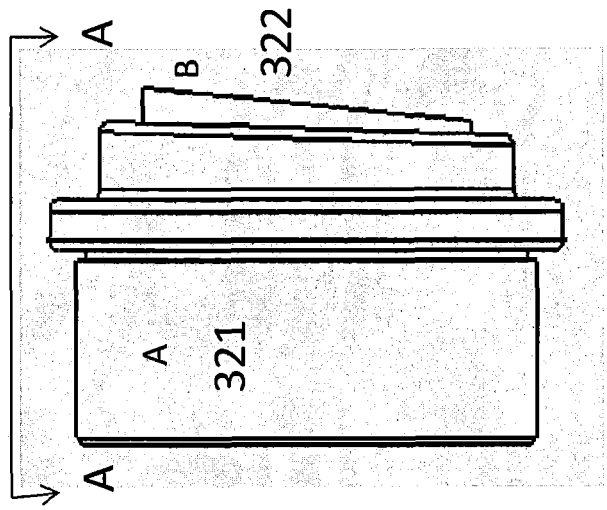
Figure 4A:
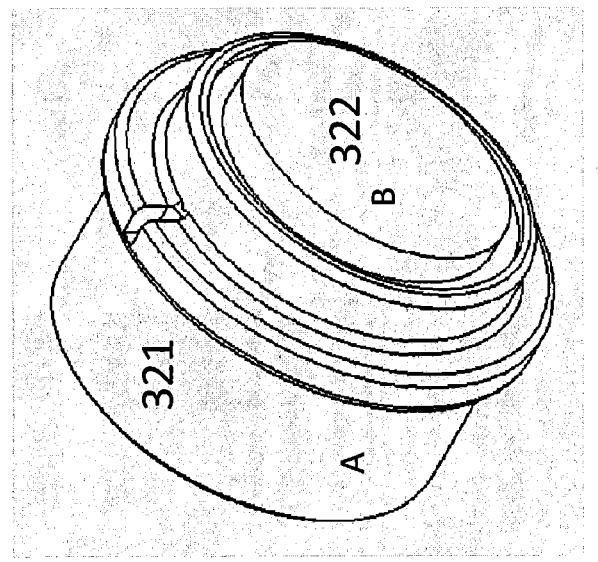

Referring now to FIGS. 4A through 4C, an isometric view, a side view and cut away view along the line A-A of FIG. 4B, respectively, of an immersion tip assembly in accordance with some embodiments of the present inventive concept will be discussed. As illustrated in FIGS. 4A through 4C, the wedge 322 is on a mount 321 that affixes to the telecentric lens. The prism window mount A and prism window B are also illustrated in FIGS. 4A-4C. As will be discussed below, the position between the wedge 322 and the imaging lens 321 is used to precisely control the focus and path matching conditions for optimum imaging.

Referring now to FIGS. 5A and 5B, a sample holder in accordance with some embodiments of the present inventive concept will be discussed. FIG. 5A is a plan view of the sample holder 250 and FIG. 5B is a cross section of the sample holder 250. As illustrated, the sample holder 250 includes a sample dish 251 (A) that contains the fluid, for example saline, for the bath. The sample under test is placed on the sample platform 252 (B). The sample platform 252 (B) is designed to reduce, or possibly minimize, specular reflections back into the OCT system. In some embodiments, the sample platform 252 (B) is a fine ground absorptive glass plate, 3 mm thick with an optical density of 5. The ground surface minimizes surface reflections and the high optical density assures absorption of light so that there is no back surface reflection.

The sample dish 251(A) rests on a sample tray 253 (C) designed to set orientation of the dish with respect to the OCT scanning beam and to catch spillover of fluid from the sample dish. The sample dish 251 sits on a quasi-kinematic mount to allow accurate replacement of the sample dish on the tray during multi-sample imaging sessions. This quasi-kinematic mount includes a central ball fiducial 254 (D) for rapid location of the dish, and includes a triad of balance points 255 (E) that sets the dish slightly above the base of the tray for easy rotation. The term quasi-kinematic is used to indicate that precision need not be perfect, and that corrections to realignment can be made using the controls of the spatial degrees of freedom already described. A true kinematic mount could be adopted where desired.

In some embodiments of the present inventive concept, the immersion tip is structured such that a distance between the center of the immersion wedge and the optical path matching position approximately equal to the maximum imaging depth of the Fourier domain imaging system. Such a relationship assures that any ghost reflections from the wedge are imaged to the edge of the Fourier domain window away from the sample under test, and not so far away that the imaginary components of the image alias into the image window in the vicinity of the sample under test.

In some embodiments of the present inventive concept, the focus is positioned a target distance from the path matching position to achieve the illumination uniformity discussed above, where the focal position is between the immersion wedge and the path matching condition, i.e., within the immersion bath where the sample is situated.

Referring now to the diagrams of FIGS. 6A and 6B, relationships between the immersion tip 110 and the sample under test 100 will be discussed. Attributes include the axial spatial relationships between the imaging lens 323, the immersion wedge 322, optical path length matching position 501 (optical path difference (OPD) equals zero) and the focus 502 of the OCT beam as illustrated in FIG. 6A. The end of the lens housing 324 provides a mechanical coupling point between the imaging lens and the immersion wedge. The imaging lens is a nominally telecentric fixed focus lens with a known working distance in air. Transmission through the immersion wedge and saline bath shifts the physical and optical path length to focus.

Figure 7:
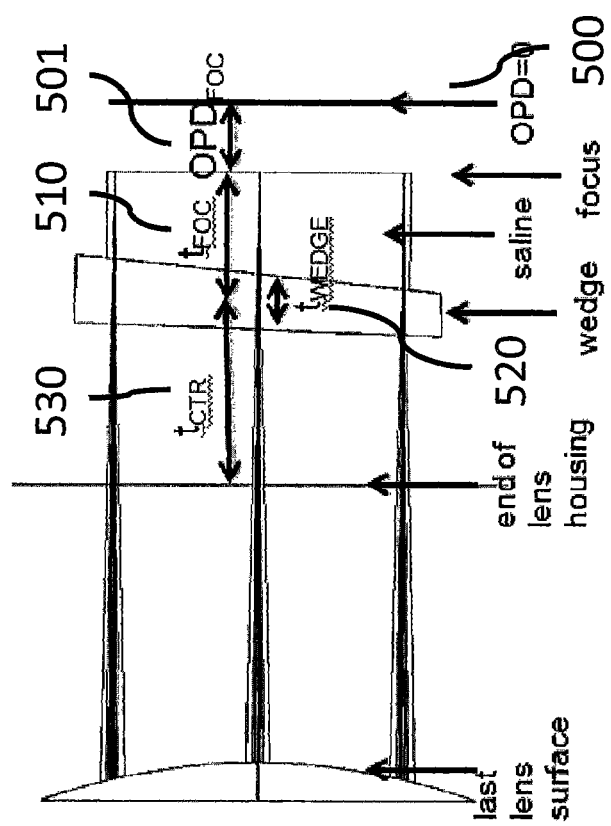
FIG. 7 is a diagram illustrating immersion tip wedge location design in accordance with some embodiments of the present inventive concept.

Referring now to FIG. 7, the relationships between the various physical parameters that impact the OCT system settings will be discussed. Defined parameters include the $t_{CTR}$ 530, the distance from the lens housing to the center of the wedge; $t_{FOC}$ 510, the distance from the center of the wedge to the position of focus; $t_{WEDGE}$ 520, central thickness of the wedge; $t_{WD}$ working distance of the lens; $OPD_{MAX}$, the maximum optical path length of the OCT image window; $OPD_{FOC}$, desired optical path length to the best focus location (as measured from the path matched position); $n_{SALINE}$, the refractive index of the saline bath; and $n_{BK7}$, the refractive index of the wedge.

In some embodiments of the present inventive concept the imaging lens has a back focal distance of 37.85 mm, as measured from the distal lens surface to focus in air, a working distance of 18.6 mm measured from the distal edge of the lens barrel to the focus in air, a wedge as described above, a saline bath with refractive index as describe above. An Equation that may be used to compute the distance between the edge of the lens barrel to wedge center, $t_{CTR}$, for a target focal position with respect to the optical path matching condition is set out below in Eqn. 1. An equation that may be used to calculate the distance to focus $t_{FOC}$ as measured from the immersion wedge given a maximum imaging widow depth ($OPD_{MAX}=z_{MAX}$ and an offset to the focal position ($OPD_{FOC}$), where OPD refers to the optical path length as measured in the medium of the bath is set out below in Eqn. 2.

$$t_{CTR} = t_{WD} + \frac{t_{WEDGE}}{2} - \frac{(t_{FOC} - t_{WEDGE}/2)}{n_{SALINE}} - \frac{t_{WEDGE}}{n_{BK7}} \quad \text{Eqn. 1}$$

$$t_{FOC} = \frac{(OPD_{MAX} - OPD_{FOC})}{n_{SALINE}} \quad \text{Eqn. 2}$$

In some embodiments, an offset between the edge of the lens barrel and the center of immersion wedge of 12.6 mm, with the distance between the wedge and the path match condition set to the OCT image window depth, will place the focus 3 mm shallower to than the path matching position.

It will be understood that accuracy in depth measurements of the immersed sample will be directly dependent on the refractive index of the immersion bath. The refractive index of the bath can be accurately determined by placing a translucent subject of known refractive index and known dimension into the bath, and measuring the step observed in the position of the substrate (FIG. 1, 132). In some embodiments of the present inventive concept, two test artifacts, one having a refractive index of 1.403 and one having a refractive index of 1.423, were imaged and the step measured to ascertain the refractive index of the bath. The bath (Equate Multi-Purpose solution, isotonic 0.9% concentration) was determined to have a refractive index of 1.343 at the imaging wavelength.

In some embodiments, a 20 mm aperture telecentric lens is used with a back focal distance (last lens to focus) of 37.85 mm and a working distance (housing to focus) of 18.6 mm. To calculate the spacing to wedge $t_{CTR}$ is the distance from lens housing to center of wedge; $t_{FOC}$ is distance from center of wedge to focus in saline bath; $t_{WEDGE}$ is thickness of wedge (on optical axis) (=3.86 mm); $t_{WD}$=lens working distance (=18.6 mm); $OPD_{MAX}$=maximum optical path length of OCT window (=15.3 mm); $OPD_{FOC}$=desired optical path length to best focus location (=3 mm); $n_{SALINE}$=index of refraction of saline (=1.343); $n_{BK7}$=index of refraction of BK7 (=1.509). For an $OPD_{FOC}$ of 3 mm, $t_{CTR}$=12.6 mm.

Thus, for the wedge Design example, the Wedge angle would be 3.88°; the first surface angle would be 2.05°; the second surface angle would be 5.93°) and the material would be N-BK7, n=1.509.

Some embodiments of the present inventive concept provide methods for accurate and precise lateral calibration of an OCT system. With the physical geometry set to meet the objectives as discussed above, the system may be calibrated. The system is calibrated in the in-use state, with a calibration artifact placed in the bath, and imaged through the immersion tip. In some embodiments of the inventive concept, the calibration artifact is a precision chrome-on-glass array of 125 μm dots on 250 μm centers over a 25 mm FOV. The array is imaged at OCT focus in direct detection mode (with the reference arm blocked), sampled at a density of 100 samples per millimeter (10 micrometer sample spacing), yielding an en face OCT image of 2001×2001 pixels.

The initial sampling was conducted using a preliminary calibration to approximate position using a linear relationship between the voltage applied to the scanning galvo mirror and the galvo mirror, converted to lateral position according the known relationships of f-theta optics. This initial approximation is corrected by a polynomial correction, and more specifically by a binomial expansion that couples the two lateral dimensions of the image.

Figure 8B:
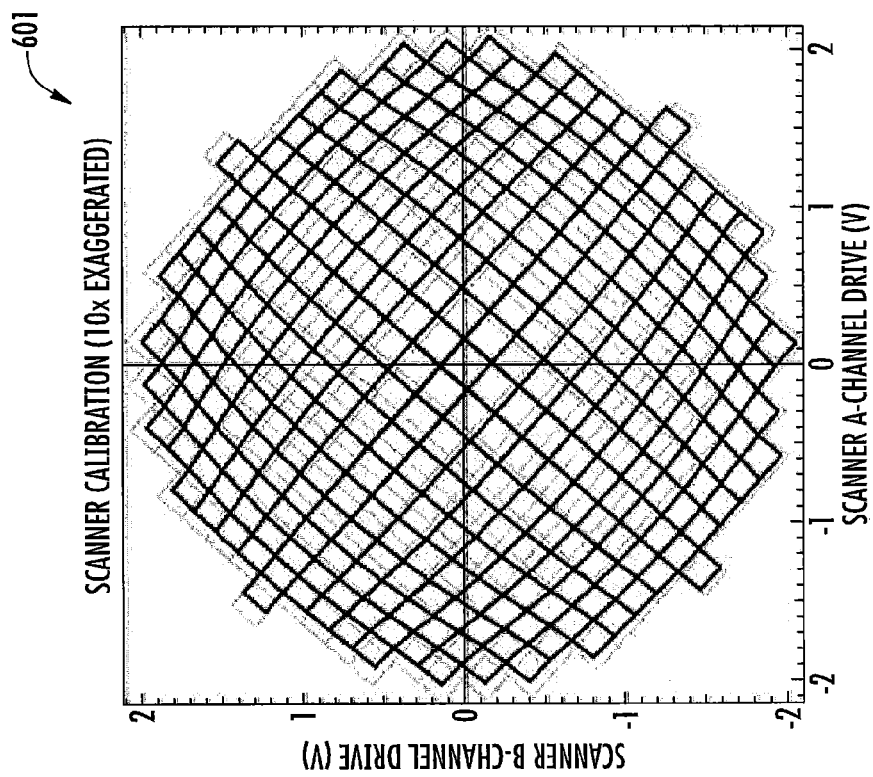
FIGS. 8A and 8B are diagrams illustrating lateral calibration of both raw (FIG. 8A) and magnified (8B) results in accordance with some embodiments of the present inventive concept.
Figure 8A:
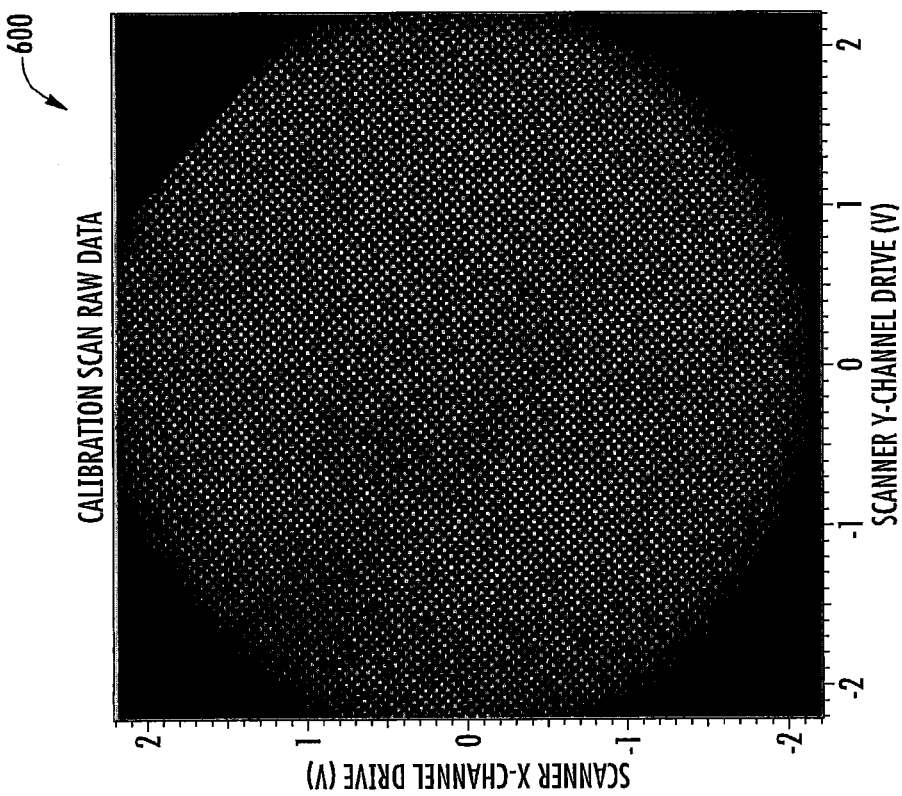

Referring now to FIGS. 8A and 8B, an acquired calibration grid is mapped to the true position of the grid, to assign true positional values to each imaged grid element. FIG. 8A 600 is an en face projection of OCT data acquired in the imaging of a high density precision grid, plotted as a function of galvo drive voltages rather than expected position. FIG. 8B 601 is 10× magnification showing the grid positions as imaged overlaid on the expected grid positions, where the barrel-like distortion is evident. The imaged positions reflect an error between the imaged pixel positions and the actual positions of the calibration artifact.

Figure 9B:
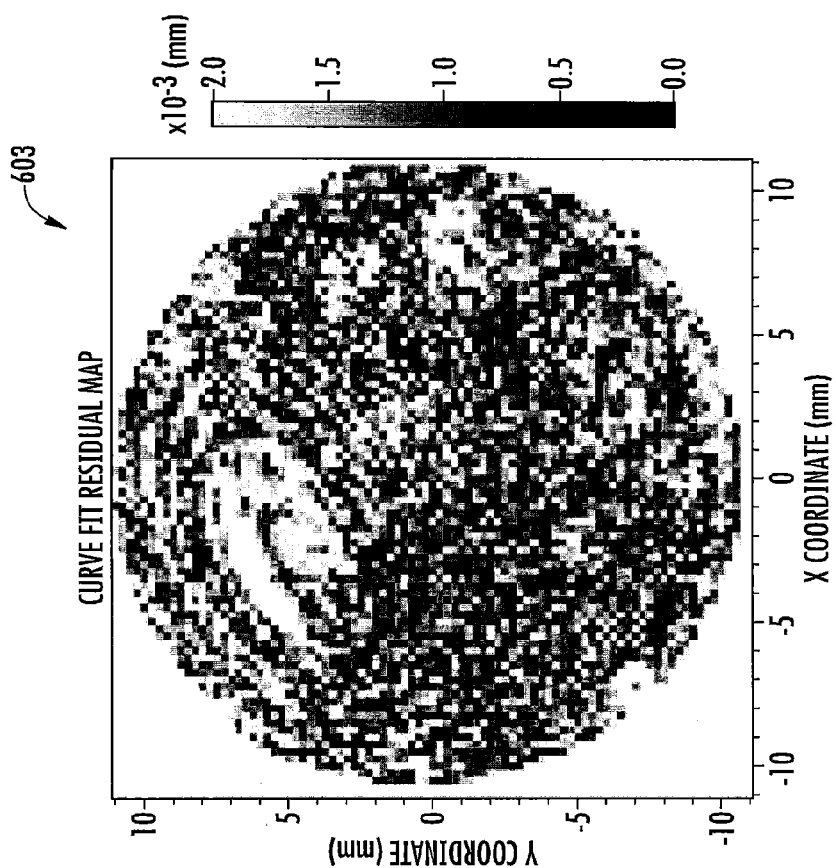
FIGS. 9A and 9B are diagrams illustrating lateral calibration including both a thresholded scan (9A) and a curve fit residual (9B) in accordance with some embodiments of the present inventive concept.
Figure 9A:
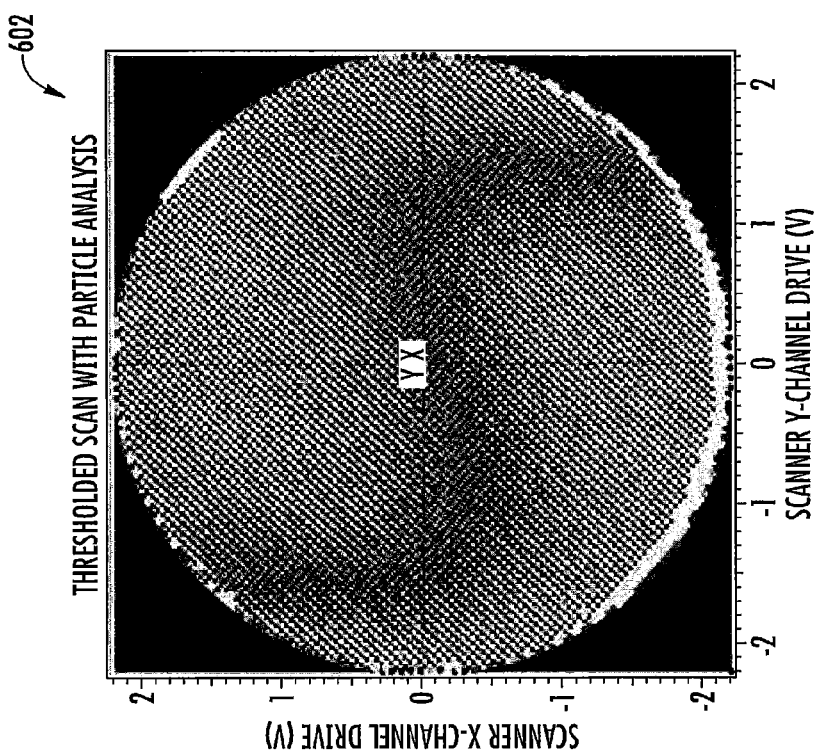
Figure 10B:
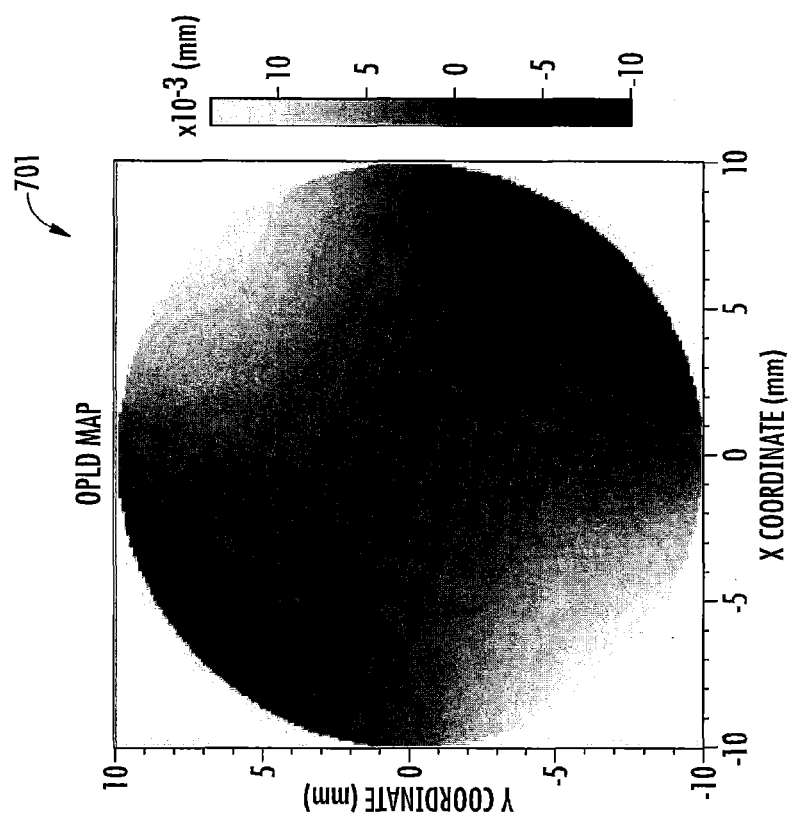
FIGS. 10A and 10B are diagrams illustrating longitudinal calibration of optical path length difference (OPLD) (μm) relative to optical axis providing a plot along four meridians (10A) and a field of view map (10B) in accordance with some embodiments of the present inventive concept.
Figure 10A:
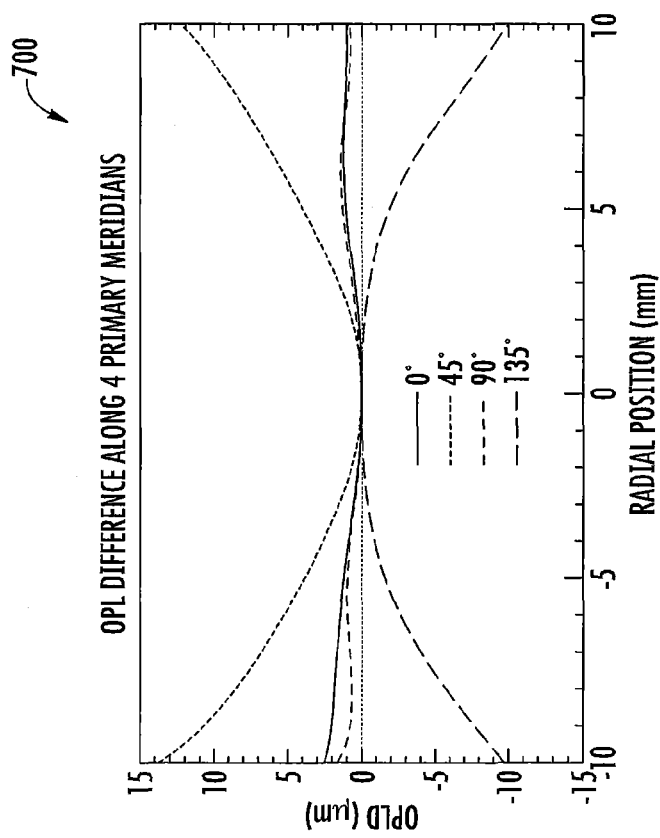

The en face image of the dot grid is cleaned up to discard any erroneous data points that could throw off the final calibration curve. The image intensity profile is normalized and thresholded, and all resultant points analyzed for ellipticity and center of mass. As the calibration artifact has perfectly circular dots, and image elements that deviate significantly from circularity and size may be discarded; it is preferable to discard good points, than to further process erroneous data. A resulting cleaned image is shown in FIG. 9A 602.

The actual known positions of dots are functionally assigned to the drive voltage these drive voltages are fit to binomial function in x and y of any arbitrary order n including all terms $x^u*y^w$, where u+w=n. In some embodiments, the grid is fit to a binomial function of order 7. With such a fit, the dot centers are located with an accuracy of plus or minus 1 μm, as shown in the residual map of FIG. 9B 602.

With the calibration function determined, a new voltage drive function for the specific geometry may be programmed into the scanning software, so that scan position is an accurate function of applied voltage. The software, rather than defining V1 and V2 drive voltages as uncoupled linear functions of desired scan positions x and y, sets each voltage (V1,V2) as a summed binomial function G(x,y;n) as determined through the calibration. The equations are of the form V1=G1(x,y;n) and V2=G2(x,y;n) where G1 and G2 are summations over binomial expansions in x and y to order n.

For example:

$$V1 = \sum_{k=0}^{n} \sum_{j=0}^{k} G1_{(k,j)} x^j y^{k-j} \qquad \text{Eqn. 3}$$

$$V2 = \sum_{k=0}^{n} \sum_{j=0}^{k} G2_{(k,j)} x^j y^{k-j} \qquad \text{Eqn. 4}$$

where $G1_{(k,j)}$ and $G2_{(k,j)}$ are the jth coefficients in the kth order binomial expansion for the drive voltages V1 and V2, respectively.

This binomial calibration function provides an unprecedented precision in scanning accuracy. In contrast to the bicubic interpolation discussed in U.S. Patent Application Publication No. 2014/0107960 to Egea, this method provides an arbitrary level of precision determined according to the number of terms n in the expansion. Further, this calibration function is particularly and uniquely useful for calibrating systems where the lab frame(x,y) is not aligned with the scanner angular frame (theta_x, theta_y).

In some embodiments, a method for accurate and precise longitudinal distortion calibration of an OCT system is provided. In particular, once the system is laterally calibrated, the axial distortion can be calibrated. In OCT mode, or interferometric mode, an image of an optical flat is acquired with the precision lateral scan calibration as described above. This again is contrast to the teachings of Egea, which specifies mapping out longitudinal distortion by imaging a three-dimensional object. Egea, in particular, seeks to identify an angular fan distortion characteristic of non-telecentric scanning systems. This fan distortion is less important in well-designed scan systems than the optical path length variation that is a more fundamental characteristic of any scanning system in an optical system possessing group velocity dispersion.

In some embodiments of the present inventive concept, a surface map is generated that describes the variation in optical path length to each point on the surface, as shown for four meridians and for the surface across the field of view in FIG. 10A 700 and FIG. 10B 701, respectively. For a pair of balanced orthogonal (x, y) scanners, this optical path length difference (OPLD) map will generally be shaped like a saddle, but this is not a necessary condition for calibration.

As in the case of the lateral calibration, the surface map is fit to a binomial equation of arbitrary order m, such that OPLD(x, y)=B(x, y, m), where B is a binomial expansions in x and y of order m. For example:

$$OPLD(x, y) = \sum_{k=0}^{n} \sum_{j=0}^{k} B_{(k,j)} x^j y^{k-j} \qquad \text{Eqn. 5}$$

where $B_{(k,j)}$ is the jth coefficient in the kth order binomial expansion for the OPLD difference from zero as a function of calibrated positions (x y). After OPLD calibration, each voxel at position (x,y,z) may be remapped to a corrected position (x,y,z').

With the voxel positions corrected, the acquired image may be segmented using any of a variety of layer segmentation algorithms known in the art. The boundary of each layer in the sample may be identified, outliers in the segmentation identified and discarded, and the surface smoothed or fit to polynomial, binomial, or model equation as appropriate. As optical rays refract at each boundary between media of a first and second refractive indices, it is necessary to correct each layer segment for lateral position using refractive correction techniques now known in the art. With layers segmented and corrected for refraction, derived attributes of the layers, surfaces, and structures may be computed with high accuracy and precision.

As discussed briefly herein, the system consists of staging system for positioning a translucent sample (artificial lens) such as a contact lens, corneal inlays and onlays, intraocular lenses, and donor tissues for cornea transplant or the like in a hydrating bath. The stage includes a positioning platform that is expressly designed to minimize specular reflections when imaged with an optical coherence tomography imaging system. The scan head of the OCT system includes a telecentric or quasi-telecentric scan assembly terminating in an immersion lens to allow the OCT image to be acquired without surface effects of a fluid-air interface. The scan head is part of a deep imaging OCT system that provides an imaging window of sufficient depth to fully visualize the sample under test, notably with minimal signal roll off across the depth range of the image. To optimize image quality, the interferometric reference position is situated distal to the sample and the OTC focus, and the OCT focus is placed at a hyperfocal position, such that the combination of reference position and focal position yield an optimally uniform illumination of the sample throughout its depth. The system scan nonlinearity is calibrated laterally and the longitudinal optical path length variation of the system is calibrated, both with an optical flat. The calibration functions are presented as two independent sets of binomial coefficients for first determining the actual (x,y) location as a function of galvo applied voltage, and determining a longitudinal correction as a function of the (x,y) location, or now equivalently the galvo applied voltage. The refractive index of the calibration bath is determined by imaging through translucent artifacts of known refractive index and thickness and measuring the optical path length difference of the bath and the artifact.

The system as discussed above is targeted at certain translucent subjects such as contact lenses placed in a saline bath, though it may be recognized that aspects of the system may be selected for imaging a variety of subjects, in or not in an immersion bath, and the bath may be a fluid or a gas that is not saline, but is reasonably transparent to the OCT illumination. The particular staging embodiments represent one method for preparing and managing the sample, but other staging geometries are possible to accomplish the objectives of the inventive concept. The spectral domain optical coherence tomography system described is one embodiment of a low coherence interferometry system for obtaining depth resolved images. Other spectrometer design, swept source OCT implementations, and other implementations of low coherence interferometry may be applied without deviating from the inventive concept. The particular grid used to calibrate the system may be substituted with another artifact with known fiducials without deviating from the inventive concept. The binomial expansion to translate drive voltages to scan position and z-offset to drive voltages is one method for establishing calibration coefficients in a Cartesian coordinate system, but it will be recognized that other functional forms and other coordinate systems may achieve the same result without deviating from the inventive concept. Additionally, it is noted that scanning mirror systems are one way to deviate an OCT beam for scanning, and such scanning mirrors may be voltage driven or current driven or hydrollically driven or otherwise without deviating from the inventive concept, and further that the scanning may not relay on mirrors at all, and may, for example, relay on rotational prisms or other mechanism for beam displacement without deviating from the inventive concept.

Figure 11:
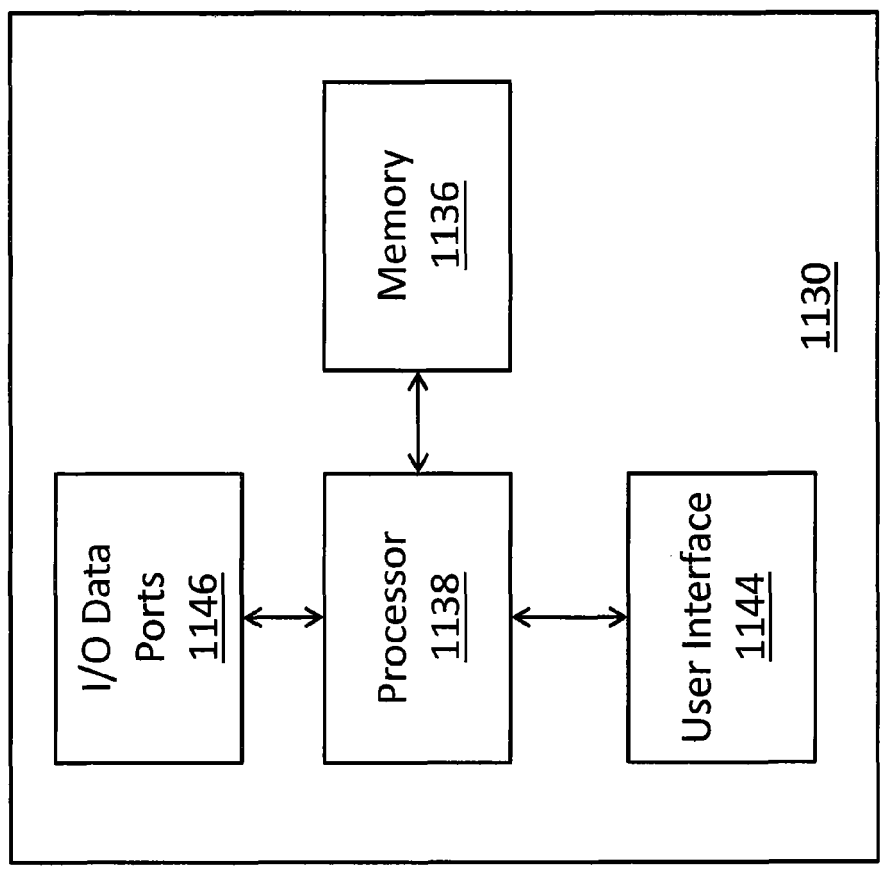
FIG. 11 is a block diagram of a data processing system that may be used to implement processes in accordance with various embodiments of the present inventive concept.

As will be understood, some aspects of the present inventive concept, for example, image processing, may be implemented by a data processing system. Exemplary embodiments of a data processing system 1130 configured in accordance with embodiments of the present inventive concept will be discussed with respect to FIG. 11. As will be understood, the data processing system may be included in the system of, for example, FIG. 2A through 2C, or may be a separate device that communications with the system in FIGS. 2A through 2C without departing from the scope of the present inventive concept. The data processing system 1130 may include a user interface 1144, including, for example, input device(s) such as a keyboard or keypad, a display, a speaker and/or microphone, and a memory 1136 that communicate with a processor 1138. The data processing system 1130 may further include I/O data port(s) 1146 that also communicates with the processor 1138. The I/O data ports 1146 can be used to transfer information between the data processing system 1130 and another computer system or a network using, for example, an Internet Protocol (IP) connection. These components may be conventional components such as those used in many conventional data processing systems, which may be configured to operate as described herein.

Figure 13:
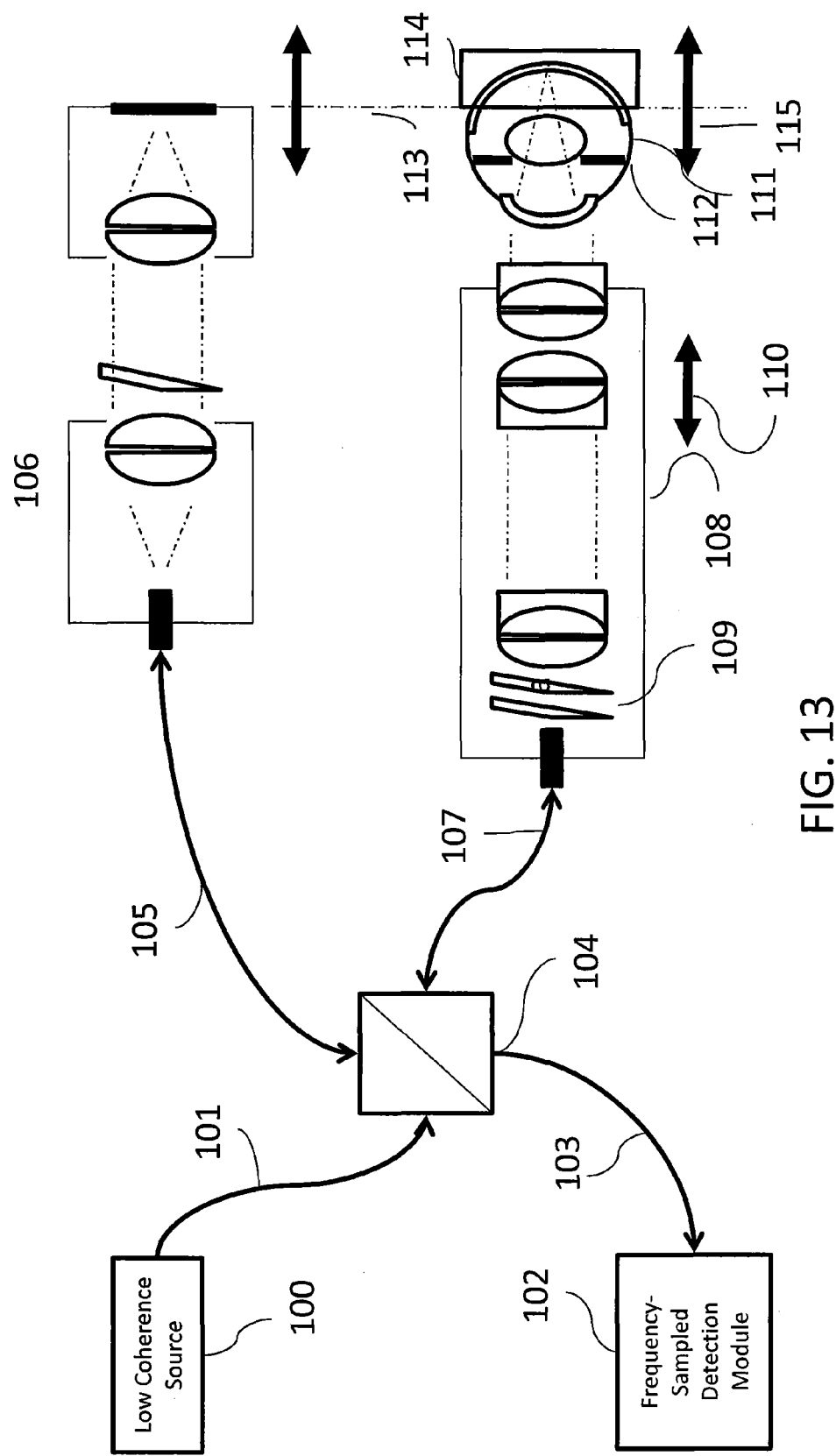
FIG. 13 is a block diagram illustrating an example OCT system that can be used in accordance with some embodiments of the present inventive concept.

Referring to FIG. 13, a Fourier domain optical coherence tomography (FDOCT) system that may be used in accordance with some embodiments of the present inventive concept will be discussed. Although embodiments of the present inventive concept are illustrated herein as using a Fourier domain optical coherence tomography (FDOCT) system, embodiments of the present inventive concept are not limited to this configuration. Any one of a variety of implementations of optical coherence tomography may be used without departing from the scope of the present inventive concept.

As illustrated in FIG. 13, the system includes a broadband optical source 100 directed along a source path 101 to a beamsplitter 104 where the source radiation is divided into a reference path 105 and a sample path 107. The reference light is returned through a reference reflection device 106 back through the beamsplitter 104, where it mixes with the light returned from a sample, such as the retina of an eye 111. The resultant wavelength dependent interferogram is directed through a detection path 103 to a detection module 102. The total spectral interferogram is processed using Fourier transforms to derive a spatial domain depth resolved image.

In contrast to a time domain OCT system, where the reference mirror scans a range over time that matches the depth range of interest for image the subject to acquire a temporal interferogram, the FDOCT system acquires a spectral interferogram from a fixed reference position 113 that is path length matched to a target axial position with respect to the subject. The spectral interferogram contains information for all depths within a window 114. The window is defined by parameters of detection as is known in the art. A scanning subsystem 108 includes a pair of scanning galvo mirrors 109 and an objective lens set with focal capabilities 110. For posterior, or retinal, ophthalmic imaging, the scanned OCT beam is directed through the pupil of the eye 112 to image the retina. An FDOCT system may include a serial acquisition of spectral information using a broadband swept frequency optical source, or a parallel acquisition of spectral information using a broadband low coherence source and a spectrometer, or a combination of these methods. A spectrometer based system is referred to as spectral domain optical coherence tomography (SDOCT) and a swept source system is referred to swept source OCT (SSOCT).

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A lens assembly for attachment to an optical coherence tomography (OCT) imaging system, wherein the OCT imaging system comprises:
    a sample arm that delivers illumination from a broadband OCT light source to a sample positioned proximate an object plane of the imaging system and includes a substantially telecentric focal system that focuses the light from the broadband OCT light source at an object plane substantially perpendicular to an optical axis of the focal system,
    wherein the substantially telecentric focal system includes a transmissive optical wedge positioned within an optical path between a focusing lens and the sample;
    wherein the optical wedge is substantially transparent across a wavelength range of the broadband optical source;
    wherein the optical wedge has a first surface and a second surface, wherein the first surface and the second surface are non-perpendicular to the optical axis of the focal system and non-parallel to the object plane; and
    wherein an angle of the first surface of the optical wedge and an angle of the second surface of the optical wedge are designed such that object space telecentricity is maintained when the subject and the object plane are within a medium having a refractive index greater than the refractive index of the medium that Is between the focusing lens and the optical wedge.

2. The assembly of claim 1:
    wherein a ray passing through the optical wedge is laterally shifted, but angularly un-deviated; and
    wherein specular reflections from the optical wedge reflect at an angle outside of a numerical aperture of an OCT beam.

3. The assembly of claim 1, wherein the optical wedge comprises an anti-reflection coating to reduce optical losses at an air-wedge interface and a bath-wedge interface.

4. The assembly of claim 1, wherein the optical wedge comprises N-BK7 glass with a refractive index of 1.509, a wedge with a first surface angle of two degrees with respect to the optical axis of the focal system and a second surface angle of six degrees with respect to the optical axis of the focal system.

* * * * *

UNITED STATES PATENT AND TRADEMARK OFFICE
CERTIFICATE OF CORRECTION

PATENT NO. : 9,733,152 B2  
APPLICATION NO. : 14/573339  
DATED : August 15, 2017  
INVENTOR(S) : Saxer et al.

Page 1 of 1

It is certified that error appears in the above-identified patent and that said Letters Patent is hereby corrected as shown below:

Column 16, Line 35, please change "Is" to -- is --.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*